United States Patent [19]

Latour et al.

[11] Patent Number: 5,580,867
[45] Date of Patent: Dec. 3, 1996

[54] MYOCARDIAL PROTECTION DURING ISCHEMIA AND REPERFUSION

[75] Inventors: Jean-Gilles Latour, Saint-Eustache; Denis Gravel, Saint-Lambert; Serge Benoît, Duvernay; Yuan Wang, Kirkland, all of Canada

[73] Assignee: Universite de Montreal, Montreal, Canada

[21] Appl. No.: 303,826

[22] Filed: Sep. 9, 1994

[51] Int. Cl.$^6$ ............................................. A61K 31/55
[52] U.S. Cl. ........................................... 514/213; 514/211
[58] Field of Search .................................. 514/213, 211

[56] References Cited

U.S. PATENT DOCUMENTS

| 4,520,112 | 5/1985 | Snyder et al. | 436/504 |
| 4,743,599 | 5/1988 | Muller | 514/211 |
| 4,902,684 | 2/1990 | Floyd | 514/211 |
| 4,950,663 | 8/1990 | Dumont et al. | 514/211 |

OTHER PUBLICATIONS

Nagao Chem Pharm. Bull 21 1, p. 92 (1973) Abst.
Tanguay J Cardiovasc. Pharmacol. 24 #6 p. 950, 1994 Abs.
Multicenter Diltiazem Postinfarction Trial Research Group, *New Eng. J. Med.*, 319:385–92 (1988).
Grover et al., *J. Pharmacology and Exp. Therapeutics*, 246:263–69 (1988).
Moss et al., *Circulation*, Supp IV, 80:102–06 (1989).
Grover et al., *J. Cardiovascular Pharmacol.*, 16:219–27 (1990).
Rousseau et al., *Cardiovascular Research*, vol. XXV, No. 4, pp. 319–329 (1991).
Goldstein et al., *Circulation* 83:52–60 (1991).
Poole–Wilson, *Am. J. Cardiology*, 75:4E–9E (1995).
Tanguay et al., *J. Cardiovascular Pharmacol.*, 24:950–59 (1994).
Kiyomoto et al., *Circ. Res.*, 52 (Supp I): 115–19 (1983).
Nasa et al., *J. Pharmacol. and Exp. Therapeutics*, 255 (2):680–89 (1990).

Bourassa et al., *Chest*, 78:1 (Supp) pp. 224–30 (Jul. 1980).
Rovelli et al., *Lancet*, Feb. 22, 1986, pp. 397–401.
Reimer et al., *Circulation*, 56 (5):786–94 (1977).
Braunwald et al., *J. Clin. Invest.*, 76:1713–19 (1985).
Schofer et al., *JACC*, 5 (3):593–98 (1985).

(List continued on next page.)

*Primary Examiner*—Gollamudi S. Kishore
*Attorney, Agent, or Firm*—Evenson, McKeown, Edwards & Lenahan

[57] ABSTRACT

Myocardial protection is achieved by administering to a patient an effective amount of a benzothiazepine derivative. The benzothiazepine derivatives have the following general chemical formula:

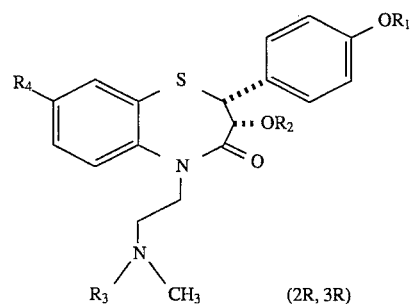

wherein
 $R_1$ represents hydrogen or methyl,
 $R_2$ represents hydrogen or acetyl,
 $R_3$ represents hydrogen or methyl, and
 $R_4$ represents hydrogen or a halogen,
 with the proviso that $R_1$ cannot be methyl when $R_2$=acetyl, $R_3$=methyl and $R_4$=hydrogen.

The above compounds may also be used in other clinical conditions such as treatment of stable and unstable angina, non-Q-wave myocardial infarction, cerebral trauma ischemia and reperfusion, organ graft preservation, etc.

4 Claims, 7 Drawing Sheets

OTHER PUBLICATIONS

Lorgeril et al., *Am. J. Cardiovascular Pathology*, 3 (2):143–54 (1990).

Rousseau et al., *J. Cardiovascular Pharmacol.*, 22:264–72 (1993).

Rousseau et al., *J. Pharmacol. and Exp. Therapeutics*, 268 (3):1252–60 (1994).

Roberts, *Circulation*, (Supp IV) 80 (6) IV:93–101 (1989).

Messerli et al., *Am. J. Cardiology*, 72:818–20 (1993).

Schwartz et al., *J. Org. Chem.*, 57:851–56 (1992).

Rousseau et al., *Am. Heart J.*, 125 (6):1553–63 (1993).

Li et al., *J. Med. Chem.*, 35:3246–53 (1992).

Product sheet for "Cardizem SR", *Medicine North America*, 36 p. 6558 (1989).

*Merck Index*, Entry 3189 "Diltiazem", 10th Ed. (1983).

MYOCARDIAL PROTECTION DURING ISCHEMIA AND REPERFUSION

BACKGROUND OF INVENTION (a) Field of the Invention

The present invention relates to a method of providing myocardial protection in a patient during ischemia and reperfusion, utilizing a benzothiazepine derivative.

(b) Description of Prior Art

Timely reperfusion of ischemic myocardium limits infarct size in the experimental animal, and clinical data collected over the past decade with thrombolytic therapy have documented the benefits of early reperfusion on myocardial damage, ventricular function and mortality in patients with acute myocardial infarction (1,2).

Myocardial salvage can however be compromised by such complications as coronary reocclusion and severe residual coronary stenosis (11). Furthermore, results of animal studies and clinical investigations have provided convincing evidences that even when vessel patency is achieved, damage still proceeds in the post-ischemic myocardium (3,4). Although it is not yet unequivocally established that reperfusion can damage normal tissue, studies have shown that reperfusion not only accelerates death of irreversibly injured myocardium, but may also compromise survival of jeopardized, but still viable myocytes salvaged by reperfusion. These so-called reperfusion injuries may represent more than 50% of ultimate infarct size (5). Development of adjuvant treatments to protect the post-ischemic myocardium and maximize benefits of coronary reperfusion has thus become a major target of modern cardiovascular research.

With tissue reoxygenation, calcium-dependent mechanisms can mediate tissue damage through generation of oxygen derived radicals. A significant source of free radicals is the neutrophil which also releases lysosomal enzymes mediating cell destruction and vessel damage. Neutrophils and platelets accumulate in the reperfused territory and particularly at the edge of the infarct and the salvaged myocardium (5, 8, 11). These inflammatory cells accumulate at the wrong place and at the wrong time compromising recovery of reversibly injured myocardium salvaged by early reperfusion.

In the past years, it has been demonstrated that some benzothiazepine calcium antagonists given at the time of reperfusion, at therapeutic doses, after coronary occlusion, protect the reperfused myocardium, reducing infarct size permanently by more than 40% (6–8).

These conditions and observations could not be met or reproduced by some other calcium antagonists, suggesting that additional effects than blockade of slow-L calcium channels is likely involved in the protective mechanism. The cardio-protection was observed at dosages having no effect on cardiac work load, as estimated by the .pressure rate product, and was accompanied by improvement of the no-reflow or the circulatory failure developing in the reperfused ischemic myocardium, at doses having no measurable direct coronary vasodilating effects. Finally, it was demonstrated that these agents were preventing neutrophil accumulation in the post-ischemic myocardium.

The results led to the conclusion that some calcium antagonists could be useful in patients with acute myocardial infarction undergoing thrombolytic therapy. However, recent clinical trials have documented the risks and benefits of calcium antagonists in post-myocardial infarction patients (9, 10). Those acting on afterload are not recommended and others like diltiazem offer protection against reinfarction only in subgroups of patients. Considering the above data, Applicant searched for benzothiazepine derivatives with cardioprotective effects and possessing no cardiodepressive nor hypotensive effects that could limit their use in the set up of acute myocardial infarction and thrombolytic therapy.

It is an object of the present invention to provide a substance which can reduce infarct size at doses having no significant direct vasoactive action.

It is another object of the present invention to provide a method of ensuring myocardial protection in a patient during ischemia and reperfusion.

SUMMARY OF THE INVENTION

These and other objects of the invention may be achieved in a method of providing myocardial protection in a patient during ischemia and reperfusion, which comprises administering to said patient an effective amount of (2R, 3R)-2, 3-dihydro -3-hydroxy-2-(4-methoxyphenyl)-5-[2-(methylamino)ethyl]-1,5-benzothiazepin-4(5H)one or derivatives thereof. For the sake of brevity and convenience, the above benzothiazepine derivative or a salt thereof will be referred to in the present description as protectazem.

Preferably, protectazem salts or derivatives thereof are administered, most advantageously by intravenous injection, after coronary occlusion up to a few minutes before coronary reperfusion, during reperfusion, and potentially before ischemia.

In accordance with another embodiment of the invention, protectazem is administered at doses which vary between about 20 and about 200 mg or more depending on body weight adjustments and future data from pharmacologic and pharmacodynamic studies in humans.

The compound protectazem which stands for (2R,3R)-2, 3-dihydro-3-hydroxy-2-(4-methoxyphenyl) -5-[2-(methylamino)ethyl]-1,5-benzothiazepin-4(5H)-one has been documented as Registry No. 86408-40-4 but its synthesis and physical characteristics have not been reported. The compound may be represented by the following structural formula:

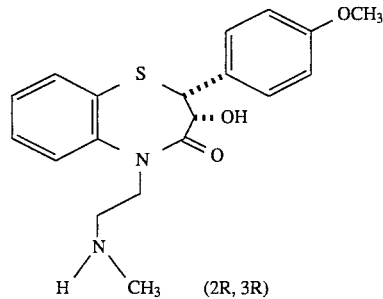

This compound is now characterized as its hydrochloride by the following: m.p. 208°–209° C.; $[\alpha]D^{23}$–122.8° (0.5, $H_2O$).

In accordance with the invention, protectazem may be prepared by condensing trans methyl 3-(4-methoxyphenyl)glycidate with 2-aminothiophenol to give the compound methyl 3-[(2aminophenyl)thio]-2-hydroxy-3-(4-methoxyphenyl) propionate in its racemic form, saponifying the latter with methanolic aqueous sodium hydroxide to give the corresponding racemic acid 3-[(2aminophenyl)thio]-2-hydroxy-3-(4-methoxyphenyl) propionic acid, resolving the latter racemic acid using (S)-(-)-α-methylbenzylamine to give the optically pure compound (2R,3R)-3-[(2-aminophenyl)thio]-2-hydroxy-3-(4-methoxyphenyl)propionic acid, cyclizing the latter compound to give (2R,3R)-2,3-dihydro-3-hydroxy-2-(4-methoxyphenyl)-1,5-benzothiazepin-4(5H)-one, which is then alkylated with benzyl (2-chloroethyl) methylcarbamate to give (2R,3R)-5-[2-[N-benzyloxycarbonyl)-N-methylamino]ethyl]-2,3-dihydro-3-hydroxy-2-(4-methoxyphenyl)-1,5-benzothiazepin-4(5H)-one, and finally deprotecting the latter compound into the free amine form (2R,3R)-2,3-dihydro-3-hydroxy-2-(4-methoxyphenyl)-5-[2-(methylamino)ethyl]-1,5-benzothiazepin-4(5H)-one, which is optionally transformed into its hydrochloride.

In accordance with a broader aspect, the invention relates generally to compounds of the general formula:

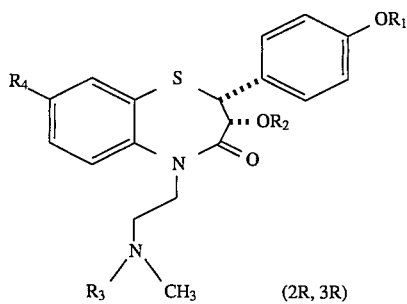

wherein:
  $R_1$ represents hydrogen or methyl,
  $R_2$ represents hydrogen or acetyl,
  $R_3$ represents hydrogen or methyl, and
  $R_4$ represents hydrogen or a halogen,
with the proviso that $R_1$ cannot be methyl, when $R_2$=acetyl, $R_3$=methyl and $R_4$=hygrogen.

These compounds can be used similarly as protectazem in providing myocardial protection in a patient during ischemia and reperfusion and may be prepared by a similar process as the one defined above for protectazem.

The invention is illustrated but not limited by the specific preparation of protectazem given below with an accompanying flow chart depicting the various reactions involved.
Methyl 3-[(2-aminophenyl)thio]-2-hydroxy-3-(4-methoxyphenyl) propionate (2).

Dissolve methyl 3-(4-methoxyphenyl)glycidate 1 (246.1 g, 1.182 mol) in toluene (2.2 L) and add 2-aminothiophenol (148.0 g, 1.182 mol). Reflux under nitrogen for 6 h and concentrate the solution to ⅓ volume. Allow the mixture to cool and add a solution of 50% hexanes/ether (100 mL). Let stand overnight to precipitate. Filter, wash the solid with 70% hexanes/ether and dry in vacuo to obtain the title compound 2 (295.6 g, 75%). m.p. 91°–93° C.
3-[(2-Aminophenyl)thio]-2-hydroxy-3-(4methoxyphenyl) propionic acid (3).

Dissolve the aminoester 2 (198.3 g, 594.6 mmol) in methanol (300 mL) and heat to reflux. Cautiously add a hot solution of sodium hydroxide (26.72 g, 1.1 equiv) in water (300 mL). Reflux for 20 min and concentrate in vacuo. Add water (300 mL) and wash with chloroform (3×50 mL). Separate the aqueous phase and neutralize with 10% HCl to pH 5.0 (pH meter). Filter and wash the solid with water then with cold ethanol. Dry in vacuo at 40° C. to obtain the racemic acid 3 (161.5 g, 85%). m.p. 174°–176° C.
(S)-α-Methylbenzylammonium (2R,3R)-3-[(aminophenyl)thio]-2-hydroxy-3-(4-methoxyphenyl) propionate (4).

Dissolve the racemic acid 3 (81.7 g, 255.8 mmol) in 1N sodium hydroxide (261 mL, 1.02 equiv) and add water (174 mL). Heat the mixture to reflux.

Dissolve (S)-(-)-α-methylbenzylamine (14.6 g, 0.47 equiv) in 1N HCl (122 mL, 0.48 equiv) and heat to about 80° C.

Add the second solution to the first and reflux for 2 min. Cool the mixture to room temperature and then allow to stand at 0° C. for 2 h. Collect the crystals by filtration and wash with cold water. Recrystallize with 50% aqueous ethanol to obtain the pure title compound 4 (45.1 g, 40%). m.p. 159°–160° C. $[\alpha]_D^{23}$ –463.8° (1.3, DMF).
(2R,3R)-3-[(2-Aminophenyl)thio]-2-hydroxy-3-(4-methoxyphenyl)propionic acid (5).

Dissolve the (-)-salt 4 (42.85 g, 97.26 mmol) in boiling water (430 mL). Add hot 1N HCl (98 mL). Reflux for 1 min. Cool the mixture in an ice-water bath and stir vigourously to precipitate. Check (and adjust if necessary) the pH of the solution to 5.0 (pH meter). Collect the solid by filtration. Wash with water and dry in vacuo at 40° C. to obtain the title compound 5 (24.85 g, 80%). m.p. 175°–176° C. $[\alpha]_D^{23}$ –362.8° (1.2 DMF).
(2R,3R)-2,3-Dihydro-3-hydroxy-2-(4-methoxyphenyl)-1,5-benzothiazepin-4(5H)-one (6)[12].

Add p-toluenesulfonic acid (974 mg) to a mixture of the (-)-acid 5 (32.7 g, 102.4 mmol) and xylenes (400 mL). Reflux under nitrogen for 16 h, using a Dean-Stark trap to remove water. Cool the reaction mixture to 0° C. to precipitate. Filter and wash the solid with a cold solution of 80% hexanesether. Recrystallize in isopropyl alcohol to obtain the pure title compound 6 (24.42 g, 86%). m.p. 203°–205° C. $[\alpha]_D^{23}$ –56.0° (0.22, CHCl₃); –112.2° (1.15, DMF).
(2R,3R)-5-[2-[N-(benzyloxycarbonyl)-N-methylamino]ethyl]-2,3-dihydro-3-hydroxy-2-(4-methoxyphenyl)-1,5-benzothiazepin-4(SH)-one (8).

Wash potassium hydride (35% in oil, 10.6 g) with pentane and add anhydrous DMF (330 mL). Add the solid (-)-lactam 6 (26.53 g, 88.02 mmol) by portions to allow a steady evolution of hydrogen. Stir for 5 min after addition.

Add benzyl (2-chloroethyl)methylcarbamate 7[13] (24.1 g, 1.2 equiv.) to the above reaction mixture- Rinse the container with DMF (20 mL) and add to the reaction mixture. Stir at 60° C. for 18 h. Concentrate in vacuo. Partition the residue between ethyl acetate and water. Wash the organic phase with water, dry (MgSO₄) and evaporate the solvent in vacuo. Purify by silica gel flash chromatography (20:80 to 100:0 ether/hexanes) to obtain the title compound 8 (32.48 g, 75%) as a resinous material.
(2R,3R)2,3-Dihydro-3-hydroxy-2-(4-methoxyphenyl) -5- [2-(methylamino)ethyl]-1,5-benzothiazepin-4(5H)-one (9) and HCl salt (10).

Dissolve 8 (25.94 g, 52.7 mmol) in dichloromethane (105 mL) and add dimethyl sulfide (104.5 mL, 27 equiv). Slowly add BF₃.Et₂O (62.9 mL, 9.7 equiv) with vigourous stirring. After 1 h add another portion of dimethyl sulfide (85 mL, 22 equiv) and stir for another 2 h. Pour the reaction mixture into an ice-cold solution of 5% NH₄OH. Adjust the pH to 8. Add dichloromethane to extract (3×150 mL). Combine the organic phases and wash with brine. Dry (MgSO₄) and evaporate the solvent in vacuo to obtain the title compound 9.

Dissolve 9 in ethyl acetate (50 mL) and cool to 0° C. Add a solution of 6.8 N HCl/isopropyl alcohol (8.5 mL, 1.1 equiv) dropwise. Stir 10 min at 0° C. to complete the reaction. Add methanol (8 mL) and heat to reflux to dissolve the precipitate. Cool slowly to room temperature then let stand at 0° C. to recrystallize. Filter and wash the solid with ethyl acetate. Dry in vacuo to obtain the pure title compound 10 (13.59 g, 65%). m.p. 208°–209° C. $[\alpha]_D^{23}$ –122.8° (0.5, H$_2$O).
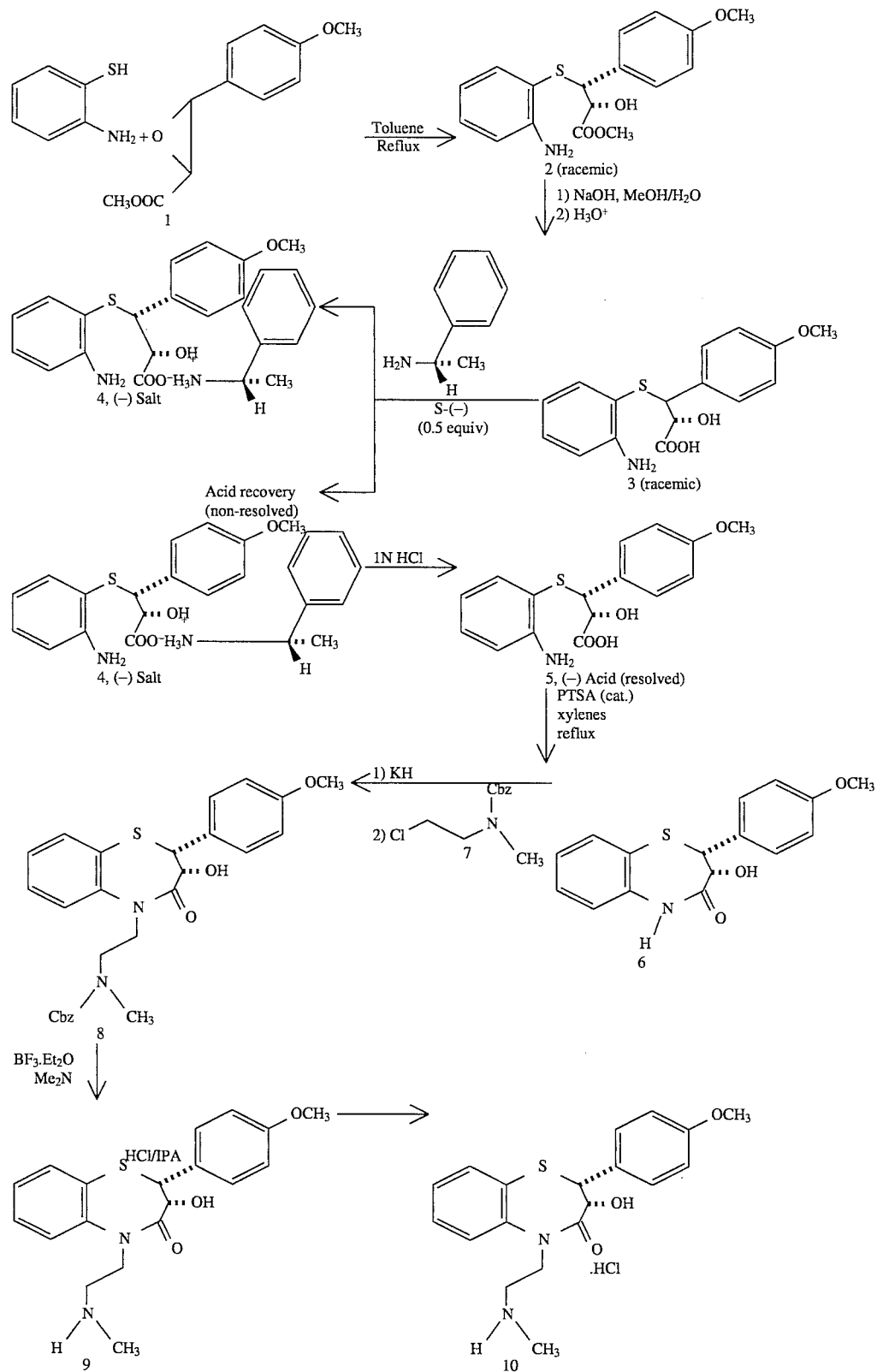

EXPERIMENTAL STUDIES

Figure 1:
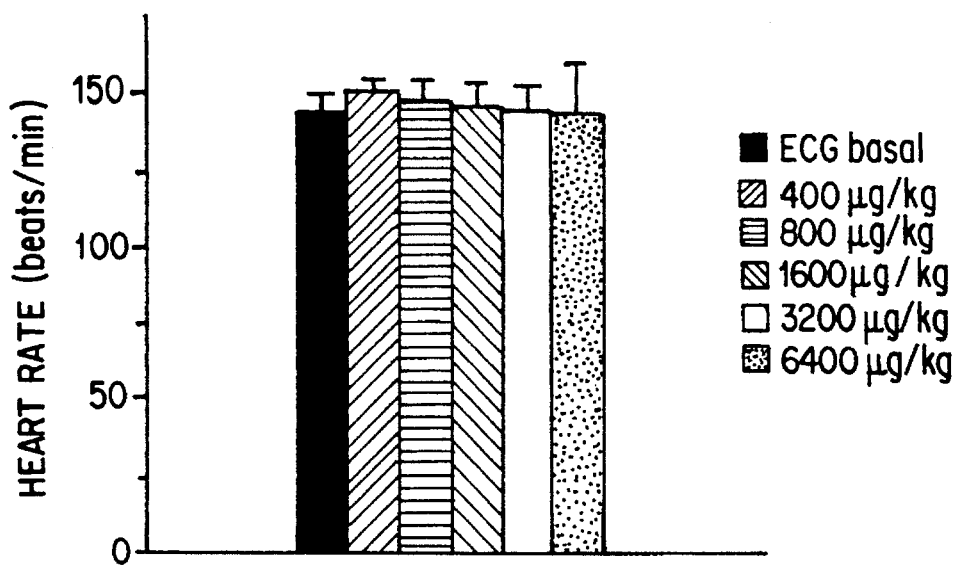
FIG. 1 is a graph showing variations of heart rate with incremental cumulative doses of protectazem.
Figure 2:
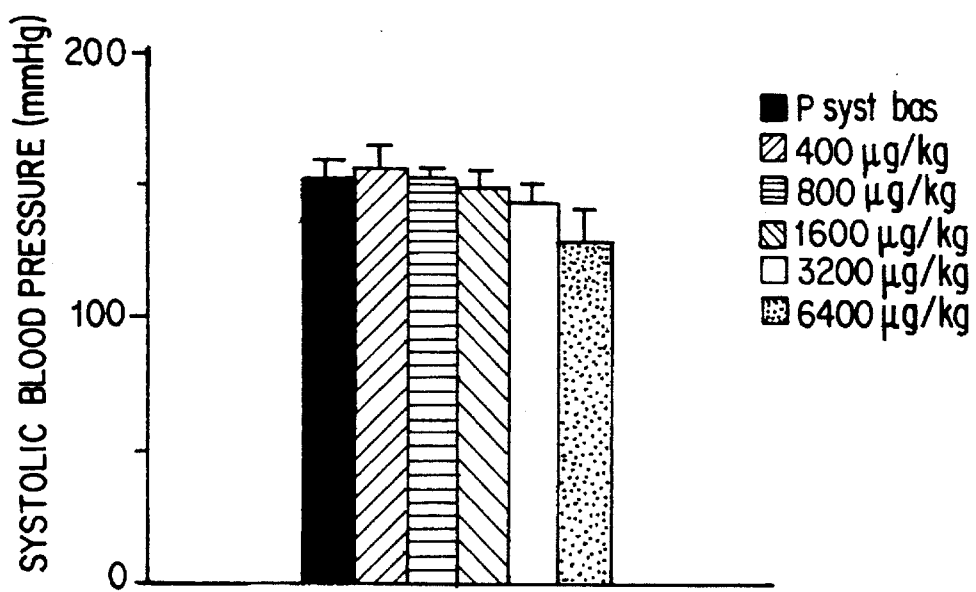
FIG. 2 is a graph showing variations systolic blood pressure with incremental cumulative doses.
Figure 3:
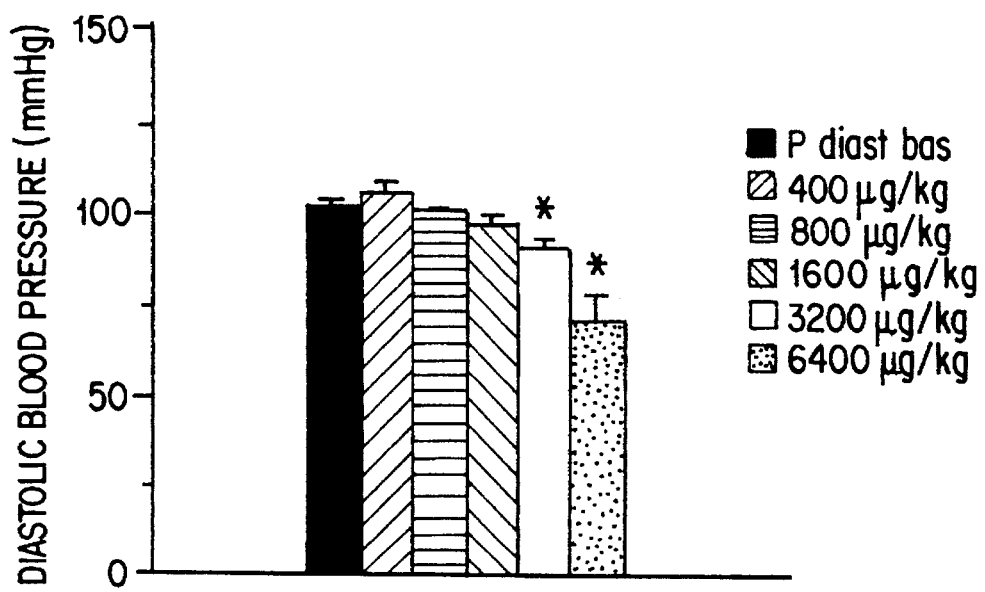
FIG. 3 is a graph showing variations of diastolic blood pressure with incremental cumulative doses.
Figure 4:
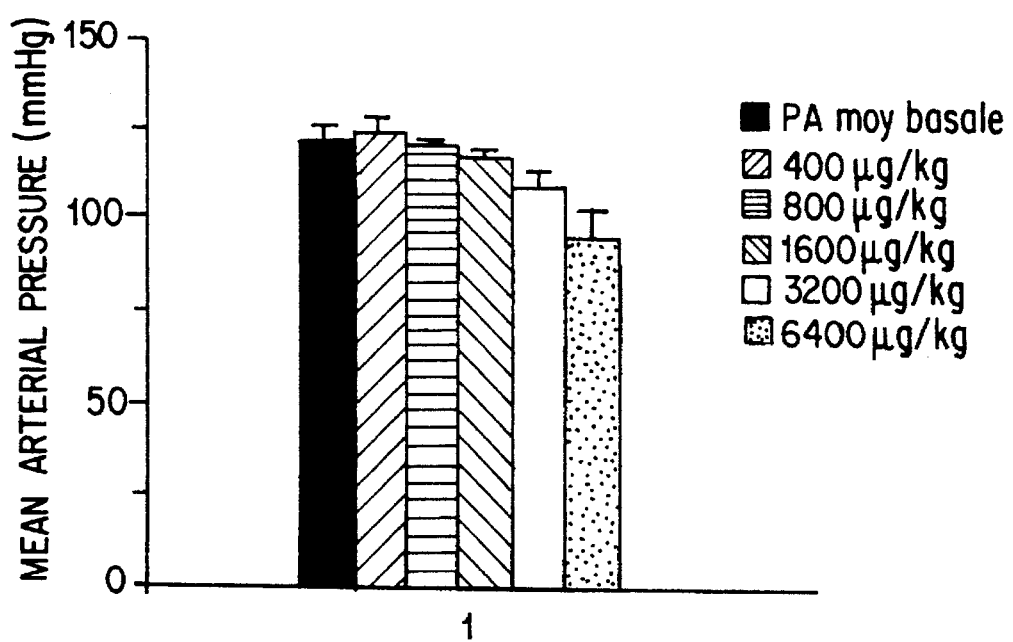
FIG. 4 is a graph showing variations in mean arterial pressure with incremental cumulative doses.
Figure 5:
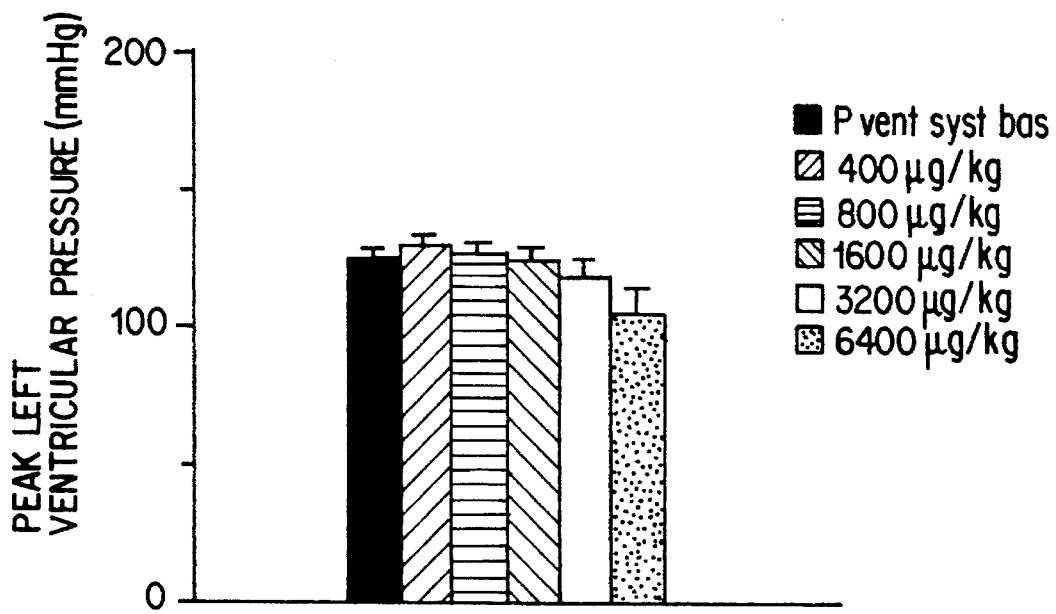
FIG. 5 is a graph showing variations in peak left ventricular pressure with incremental cumulative doses.
Figure 6:
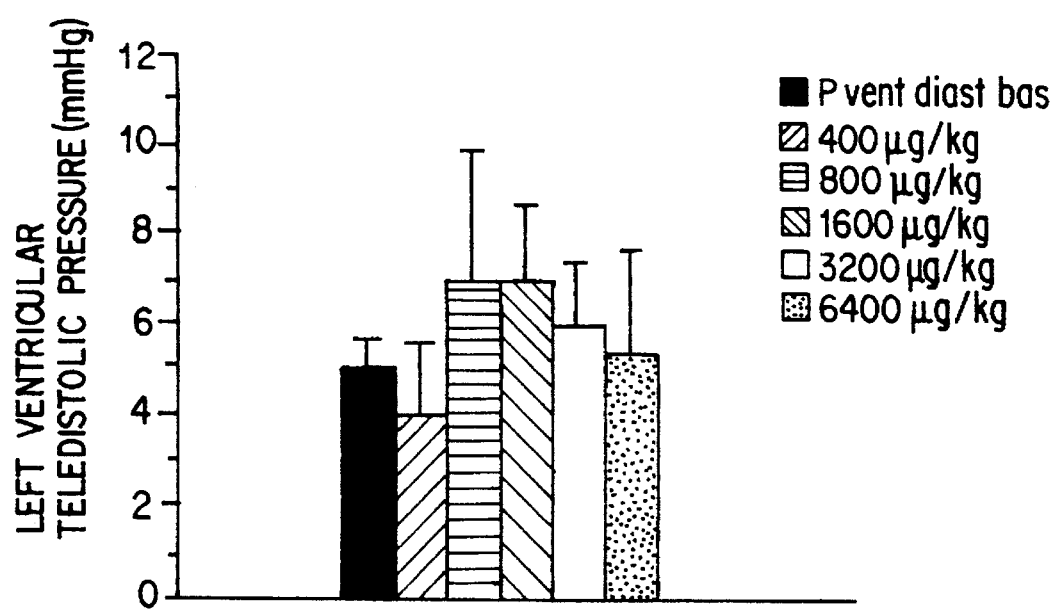
FIG. 6 is a graph showing variations in left ventricular telediastolic pressure with incremental cumulative doses.
Figure 7:
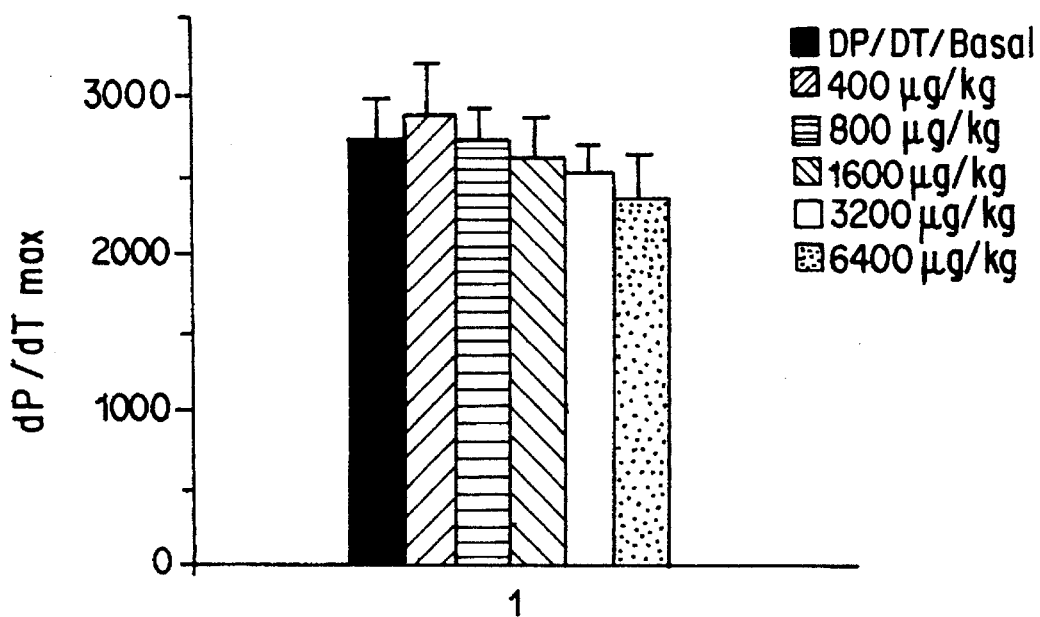
FIG. 7 is a graph showing variations in dP/dT max with incremental cumulative doses.
Figure 8:
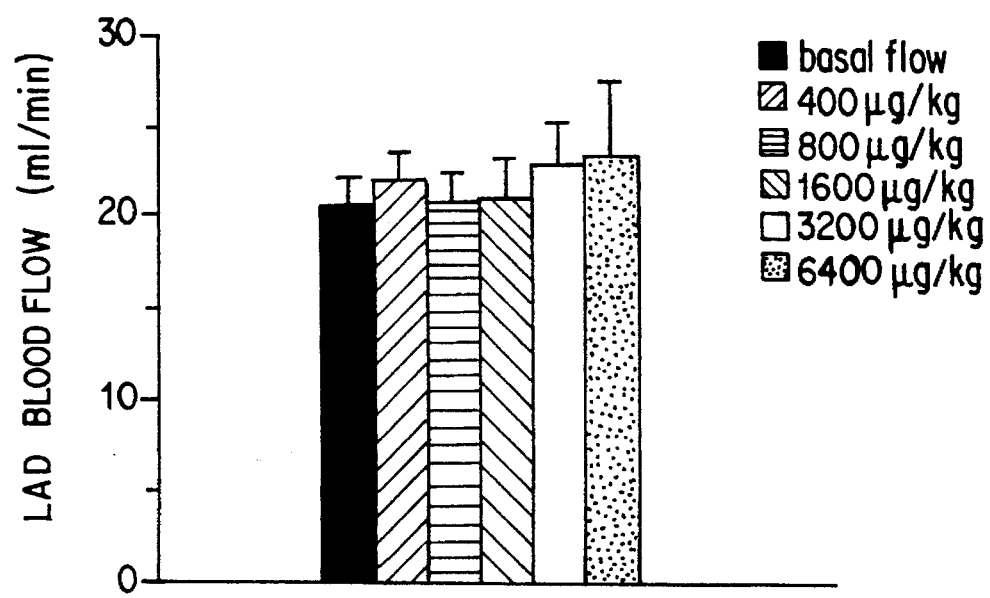
FIG. 8 is a graph showing variations in LAD blood flow with incremental cumulative doses.
Figure 9:
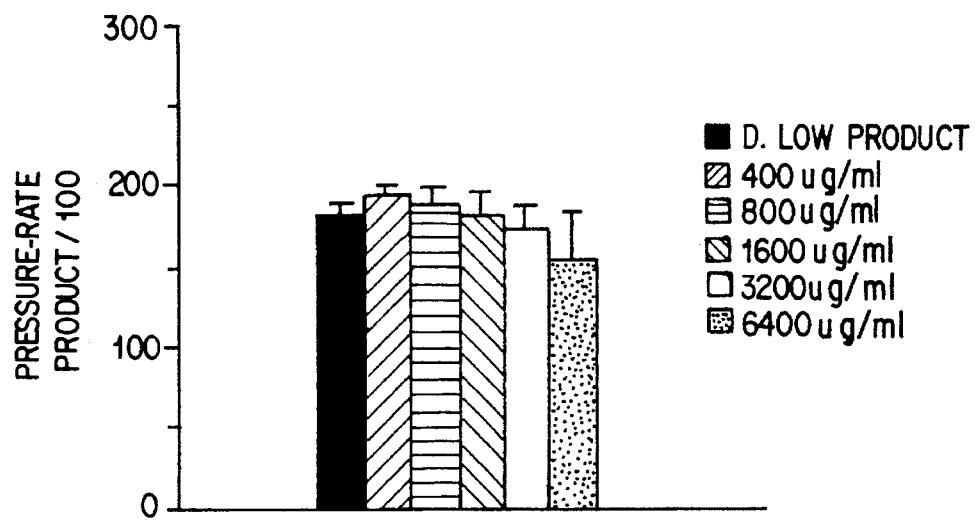
FIG. 9 is a graph showing variations in pressure-rate with incremental cumulative doses.

1. Dose-related cardiovascular effects (FIGS. 1 to 11):

Anesthetized open chest dogs were given at 15 min. intervals incremental i.v. doses of protectazem from 400 to 6400 μg/kg. Heart rate (FIG. 1), arterial systolic (FIG. 2), diastolic (FIG. 3) and mean blood pressure (FIG. 4) were monitored. Systolic ventricular (FIG. 5) and telediastolic (FIG. 6) pressures were monitored along with dP/dT (FIG. 7). Left descending coronary artery (LAD) blood flow (FIG. 8) was also measured using an electromagnetic flow probe implanted on the left anterior descending coronary artery after the first marginal branch. The pressure rate-product (systolic pressure×heart rate /100; FIG. 9) was used as the index of cardiac work load or metabolic demand.

It can be observed that protectazem had no effect on heart rate and slight hypotensive effects only at very high dosages. Myocardial contractility was unchanged as indicated by dP/dT max which was not modified by any dosage. Cardiac work load and LAD coronary blood flow were also not modified by the drug.

2. Cardioprotection in the rabbit:

Ischemia and reperfusion.

A left thoracotomy was performed in rabbits and the left coronary artery occluded for 40 min followed by 6 hours of reperfusion. Infarct size was estimated by using triphenyltetrazolium (TTC) staining after perfusing monastral blue to delimit the ischemic area at risk. Infarct size was quantified in percent necrotic area over the area at risk by planimetry after sectioning the left ventricle in 2 mm slices.

Treatment groups. After 30 min coronary occlusion or 10 min before reperfusion, a bolus i.v. injection of the agent was followed by a perfusion throughout reperfusion. Controls received physiologic saline. Doses were either 100 μg/kg bolus+perfusion of 1 μg/kg/min or multiples (2x pr 4x) of this dosage. Results are presented in FIG. 10.

Figure 11:
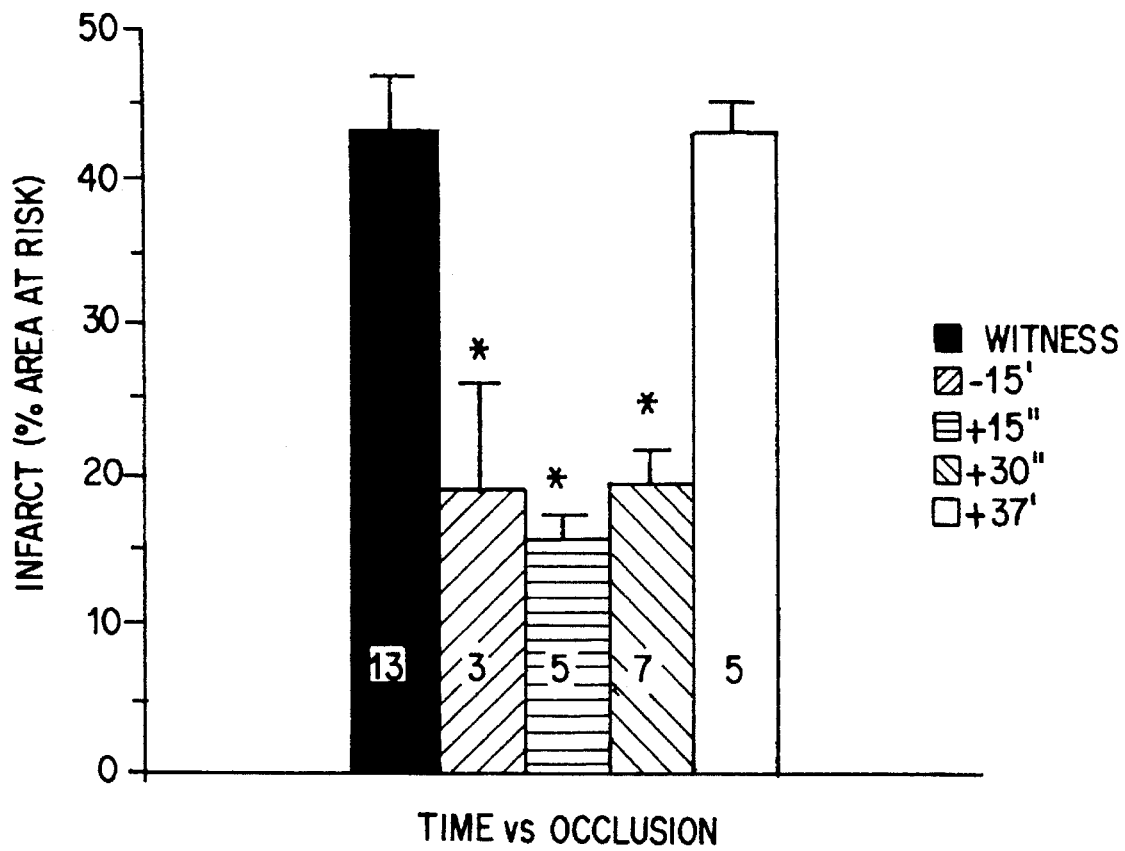
FIG. 11 is a graph of the effect of time treatment versus occlusion with different doses on infarct size in rabbits.

In a second series of experiments, the dosage of 400 μg/kg bolus+4 μk/kg/min perfusion was used. Treatments were started either before or after 15, 30 and 37 min of ischemia (FIG. 11).

Figure 10:
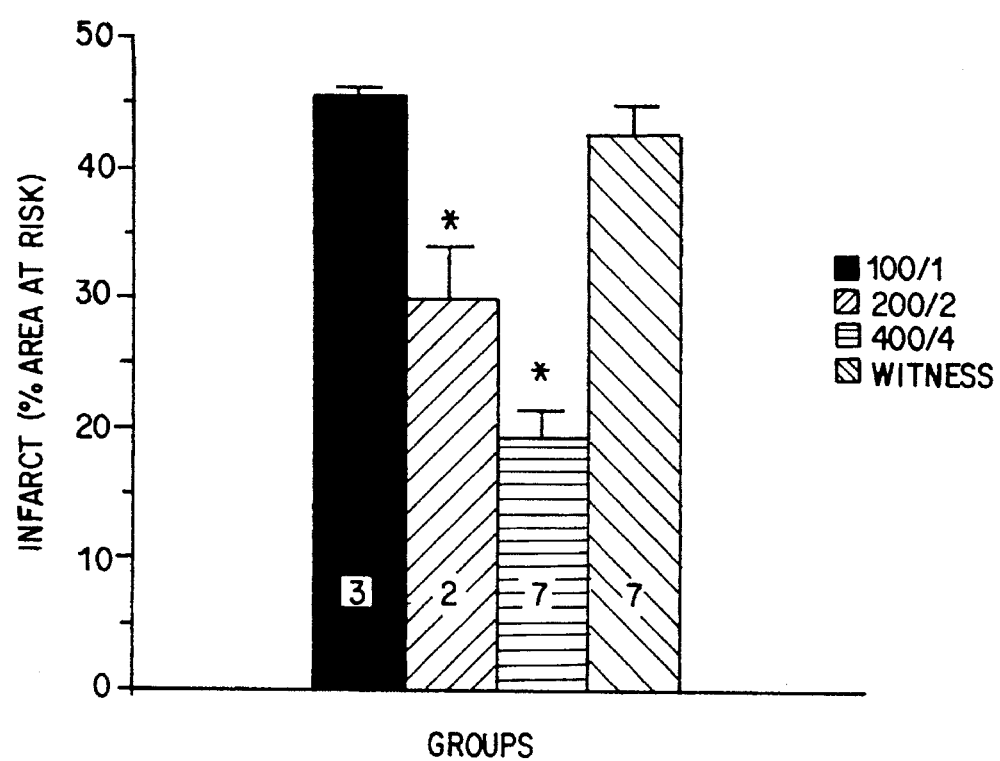
FIG. 10 is a graph showing variations in infarct size (% area at risk) with different doses.

Results:

It can be observed that a dosage of 400 μg/kg produced a 60% reduction of infarct size (P<0.05). Doses of 200 and 100 μg/kg were less effective or inactive (FIG. 10).

In series 2 experiments (FIG. 11), injecting the drug at 400 μg/kg (bolus)+perfusing 4 μg/kg/min, before or after 15 min or 30 min coronary occlusion limited infarct size by about 50% (P<0.05). However, administering the drug 3 min before reperfusion did not reduce infarct size, suggesting that, the drug must be given before reperfusion and must reach the ischemic territory in these severely ischemic preparations virtually devoid of collateral flow, to be effective.

3. Cardiooprotection in the dog.

Ischemia and reperfusion.

Mongrel dogs of either sex weighing 18 to 28 kg were anesthetized with sodium pentobarbital (30 mg/kg, i.v.), intubated and ventilated mechanically with room air. Lead II electrocardiogram was monitored, and catheters were implanted in the femoral artery and vein. After injecting pancuronium bromide (0.1 mg/kg), a left thoracotomy was performed at the fifth intercostal space, and the heart was suspended in a pericardial cradle. A catheter was placed in the left ventricle for monitoring left ventricular pressure. Another catheter was located into the left atrium for microsphere injection and blood sampling.

The LAD was isolated distal to the first diagonal branch, and an electromagnetic flow probe was installed to measure coronary blood flow. Five min before occlusion, a micrometer occluder was adjusted to produce a critical stenosis. The stenosis was sufficient to prevent the hyperaemic response produced after release of a 10-sec occlusion of the coronary. The LAD was then occluded for 90 min and reperfused for 6 hours with the critical stenosis left in place, to mimic the commonly encountered clinical situation after coronary thrombolysis for acute myocardial infarction.

Experimental design.

Animals were assigned at random between 3 groups. Controls received saline and treated dogs were given one of the following treatments: 400 μg/kg i.v.+perfusion of 4 μg/kg/min, at 10 min before reperfusion or 800 μg/kg i.v.+perfusion of 8 μg/kg/min at 15 min after coronary occlusion.

Infarct sizing.

After 6 hours of reperfusion, heparin (10,000 units) was injected i.v., and the animals were sacrificed with an overdose of pentobarbital. The heart was excised rapidly, and the site of occlusion on the LAD and the aorta above the coronary ostia were cannulated and perfused with saline (0.9%) for 5 min; subsequently, the aorta was perfused with Evans blue (Sigma Co., St. Louis, Mo.) (0.5% in saline), and the LAD with saline 0.9%, at a constant pressure of 100 mm Hg for 5 min. The left heart was then embedded in a polyurethane foam, and cut with a commercial meat slicer into 7-mm-thick transverse slices. The slices were weighed and immersed into triphenyltetrazolium chloride (TTC) for 10 min (37° C.). The normally perfused myocardium (Evans blue positive), the area at risk (Evans blue negative) and the necrotic myocardium (Evans blue and TTC negatives) were delineated, and respective areas were estimated on each slice by computed planimetry. The area at risk was expressed in percentage of the left ventricle, and infarct size was expressed in percentage of both left ventricle and the area at risk after summing values from all slices.

Regional myocardial blood flow.

Regional myocardial blood flow was estimated with the reference withdrawal method using 15-μm diameter microspheres labeled with $^{46}$Sc. Approximately 3 million microspheres, adequately dispersed in 1 ml of suspending medium containing 0.01% Tween 80®, were injected into the left atrium over 20 sec and flushed with 20 ml of saline. A reference arterial blood sample was collected from the aortic catheter at a constant rate for 150 sec, starting 15 sec before each microsphere injection. Regional blood flow was estimated after 15 min occlusion for assessment of collateral flow.

For regional myocardial blood flow analysis, four central left ventricular slices were dissected into ischemic and nonischemic parts. Sections from the central ischemic and from the non-ischemic wall opposite to the area risk were isolated and divided further into three equal subendocardial, midventricular and subepicardial portions. Each sample was weighed and counted along with reference samples in a gamma counter with selected energy windows. After correcting for background and spillover between isotopes, blood flow was estimated and expressed in ml of blood/min per g of tissue.

Figure 12:
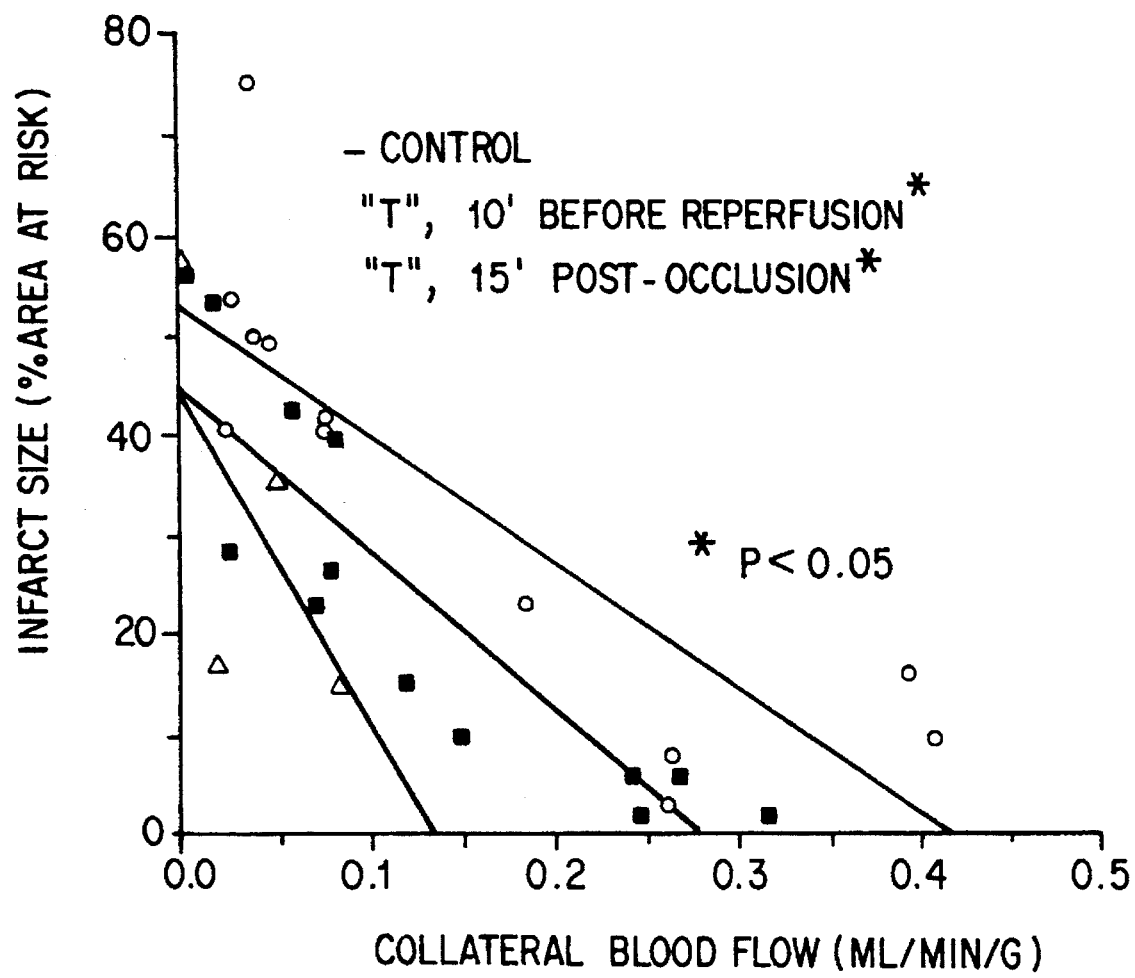
FIG. 12 is a graph showing the effect of the treatment on infarct size in the dog.

Results:

FIG. 12 illustrates the relationship between infarct size and collateral flow in the 3 study groups.

It can be observed that for a similar degree of ischemia or collateral blood flow, treated dogs developed smaller infarcts than controls, as confirmed by covariance analysis. Mean reductions of infarct size were greater than 40% with treatment at 10 min before reperfusion.

It has therefore been established that protectazem and its derivatives are potent cardioprotective agents.

The substance tested exerts no cardiovascular depressant activity limiting its use in the set up of acute myocardial infarction. It has no direct coronary vasodilator activity. It is active rapidly at low dosages after i.v. injection and is effective before, during ischemia-reperfusion. It is a highly water soluble agent.

It is believed that the compounds according to the invention have a unique cardioprotective activity profile. They constitute a new type of drug for cardioprotection offering high potentials for future clinical use in the set up of coronary thrombolysis in acute myocardial infarction.

The compounds according to the invention may also be beneficial in several other clinical conditions such as treatment of stable and unstable angina, non-Q-wave myocardial infarction, peripheral and cerebral trauma ischemia and reperfusion, organ graft preversation, etc.

Although the invention has been specifically described with reference to one compound species and one specific use, it is understood that it is susceptible to broad applications without departing from the scope and spirit of the invention.

References

1. Gissi

Effectiveness of intravenous thrombolytic in acute myocardial infarction. Lancet 1: 397–401, 1986.

2. Reimer K. A., Lowe J. E., Rasmussen M. M., Jennings R. B.

The wavefront phenomenon of ischemic cell death. 1- myocardial infarct size vs duration of coronary occlusion in dogs. Circulation 56: 786–94, 1977

3. Braunwald E., Kloner R. A.

Myocardial reperfusion: A double-edged sword? J. Clin. Invest. 76: 1713–19, 1985.

4. Schofer J., Montz R., Mathey D. G.

Scintigraphic evidence of the "no-reflow" phenomenon in human beings after coronary thrombolysis. J.Am. Coll.Cardio. 5: 593–98, 1985.

5. de Lorgeril M., Rousseau G., Basmadjian A., St-Jean G., Tran D., Latour J. G.

Spacial and temporal profiles of neutrophil accumulation in the reperfused ischemic myocardium. Am.J. Cardiovasc. Parthol. 3: 143–154, 1990.

6. Rousseau G, St-Jean G, Latour J. G., Merhi Y, Nattel S, Waters D.

Diltiazem at reperfusion reduces neutrophil accumulation and infarct size in dogs with ischemic myocardium. Cardiovasc. Res. 25: 319–29, 1991.

7. Rousseau G., Provost P., Latour J. G.

Sustained myocardial protection by clentiazem (TA-3090) after a 90 minute coronary occlusion and 72 hours of reperfusion in dogs with collateral flow. J. Cardiovasc. Pharmacol. 22: 264–72, 1993.

8. Rousseau G., Provost P., Tran D., Caillé G., Latour. J. G.

Clentiazem given at reperfusion improves subendocardial reflow and reduces myocardial infarct size in the dog. J. Pharmacol. Exp. Ther. 268: 1252–1260, 1994.

9. Roberts R.

Thrombolysis and its sequelae. Calcium antagonist as potential ajunctive therapy. Circulation 80 (suppl. IV): 93–101, 1989.

10. Messerli F. H., Weiner D. A.

Are all calcium antagonists equally effective for reducing infarction rate? Am. J. Cardiol. 72: 818–20, 1993.

11. Rousseau G., Hébert D., Libersan D., Khalil A., St-Jean G., Latour J. G.

Importance of platelets in myocardial injury after reperfusion in the presence of of residual coronary stenosis in dogs. Am. Heart J. 125; 1553–63, 1993.

12. According to the procedure of A. Schwarts described for the (2S,3S)-isomer of 6:

Schwartz, A., Madan, P. B., Mohacsi, E., O'Brien, J. P., Todaro L. J., and Coffen, D. L.

Enantioselectives Synthesis of Calcium Channel Blockers of the Diltiazem Group. J. Org. Chem. 57, 851–856, 1992.

13. Li, R.; Farmer, P. S. Xie, M. Quilliam, M. A. Pleasance, S. Howlett, S.E. and Yeung, P. K. F.

Synthesis, Characterization, and $Ca^{2+}$ Antagonist Activity of Diltiazem Metabolites. J. Med. Chem. 35, 3246–3253, 1992.

We claim:

1. A method of providing myocardial protection in a patient during ischemia and reperfusion which comprises administering to said patient an effective amount of a compound of formula:

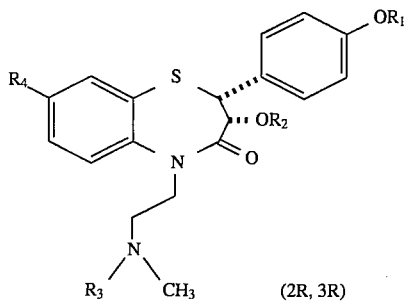

(2R, 3R)

wherein
- R₁ represents methyl,
- R₂ represents hydrogen,
- R₃ represents hydrogen, and
- R₄ represents hydrogen or a halogen, or a pharmaceutically acceptable salt thereof.

2. Method according to claim 1, wherein said compound is administered before or after coronary occlusion up to a few minutes before and during coronary reperfusion.

3. Method according to claim 2, wherein said compound is administered intravenously at doses of about 20 to about 200 mg.

4. Method according to claim 1, wherein said compound has the formula:

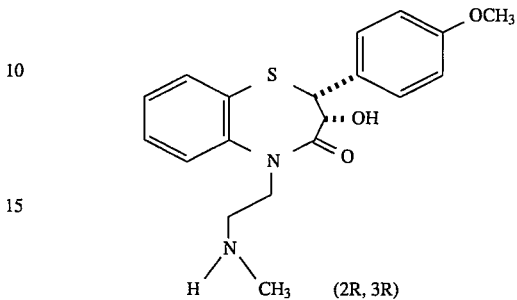

(2R, 3R)

or a salt thereof.

* * * * *